United States Patent [19]

Young

[11] Patent Number: 4,642,388

[45] Date of Patent: Feb. 10, 1987

[54] RHODIUM CATALYZED HYDROFORMYLATION OF ALPHA-SUBSTITUTED ALPHA-OLEFINS

[75] Inventor: David A. Young, Baton Rouge, La.

[73] Assignee: Exxon Chemical Patents Inc., Linden, N.J.

[21] Appl. No.: 771,429

[22] Filed: Aug. 30, 1985

[51] Int. Cl.$^4$ .............................................. C07C 45/50
[52] U.S. Cl. ..................................................... 568/454
[58] Field of Search ................................. 568/454, 909

[56] References Cited

U.S. PATENT DOCUMENTS

| | | | |
|---|---|---|---|
| 3,168,553 | 2/1965 | Slaugh | 260/497 |
| 3,239,566 | 3/1966 | Slaugh et al. | 260/604 |
| 3,511,880 | 5/1970 | Booth | 260/604 |
| 3,527,809 | 9/1970 | Pruett et al. | 260/604 |
| 3,576,881 | 4/1971 | Senn | 260/604 |
| 3,965,192 | 6/1976 | Booth | 260/598 |
| 4,201,728 | 5/1980 | Hughes | 568/454 |
| 4,221,744 | 9/1980 | Unruh | 568/454 |
| 4,277,627 | 7/1981 | Bryant et al. | 568/454 |
| 4,283,562 | 8/1981 | Billig et al. | 568/454 |
| 4,287,370 | 9/1981 | Harris et al. | 568/454 |
| 4,306,087 | 12/1981 | Matsumoto et al. | 568/454 |
| 4,443,638 | 4/1984 | Yates | 568/454 |

FOREIGN PATENT DOCUMENTS

| | | |
|---|---|---|
| 28378 | 5/1981 | European Pat. Off. . |
| 96988 | 12/1983 | European Pat. Off. . |
| 1493154 | 11/1977 | United Kingdom ................ 568/454 |

OTHER PUBLICATIONS

B. Fell et al., *Tetrahedron Letters* No. 29, pp. 3261–3266, (1968).
F. Asinger et al., *I&EC Prod. Res. & Dev.*, vol. 8, No. 2, 214, (1969).
E. R. Tucci, *I&EC Prod. Res. & Dev.*, vol. 8, No. 2, 215–216, (1969).
B. Fell et al., *J. Molec. Catalysis*, vol. 2, 211–218, (1977).
Van Leewen & Roobeek, *J. Organomet. Chem.*, vol. 258, pp. 343–350, (1983).
A. A. Oswald et al., *Preprint of Papers, American Chemical Society*, (Seattle Meeting, Mar. 20–25, 1983), vol. 2, No. 2, pp. 191–208.
R. L. Pruett et al., *JO Chem.*, vol. 34, 327, (1969).
K. L. Oliver et al., *Am. Chem. Soc. Pat. Div. Prepr., Gen. Pap.*, vol. 14 (3), 47, (1969).
C. A. Tolman, *J. Amer. Chem. Soc.*, 92, 2953, (1970).
JACS, 92, 2956, (1970).
JACS, 96, 53, (1974).
C. A. Tolman, *Chem. Rev.*, vol. 77, No. 3, 313, (1977).

*Primary Examiner*—Werren B. Lone
*Attorney, Agent, or Firm*—J. B. Murray, Jr.; J. J. Mahon

[57] ABSTRACT

Alpha-substituted alpha-olefins are rapidly hydroformylated in high selectivity to aldehyde product using homogeneous rhodium catalysts modified with highly sterically hindered tricycloalkyl phosphine ligands under mild process conditions.

22 Claims, No Drawings

RHODIUM CATALYZED HYDROFORMYLATION OF ALPHA-SUBSTITUTED ALPHA-OLEFINS

CROSS-REFERENCE TO RELATED APPLICATION

This application is related to my co-pending application Ser. No. 714,112, filed Mar. 20, 1985.

BACKGROUND OF THE INVENTION

1. Field of the Invention

This invention relates generally to rhodium catalyzed hydroformylation of olefins and more specifically to an improved hydroformylation process for alpha-substituted alpha-olefins using homogeneous rhodium catalyst systems containing highly sterically hindered tricycloalkyl phosphine ligands.

2. Description of the Prior Art

The hydroformylation of olefins to aldehydes is a widely used industrial process in which an olefin, carbon monoxide and hydrogen, are reacted in the presence of a homogeneous hydroformylation catalyst. These catalysts have historically comprised high pressure cobalt systems. Recent developments of low pressure rhodium catalyst systems have been the subject of a considerable body of patent art and literature, and rhodium-triphenyl phosphine systems have been widely, and successfully, used commercially for the hydroformylation of propylene feedstocks to produce butyraldehyde.

A large variety of trialkyl phosphines have been suggested for use in rhodium catalyzed hydroformylation of olefins. U.S. Pat. No. 3,168,533 relates to the hydroformylation of olefins (including alpha and internal monoolefins and diolefins) using Group VIIIb transition metal (Co, Ru, Rh and Ir) catalyst systems and triorganophosphorus ligands including trivalent phosphorus compounds having aliphatic, cycloaliphatic, heterocyclic and/or aromatic radicals satisfying the three valences of the trivalent phosphorus atom, at preferred carbon monoxide pressures of 5500 to 21,000 kPa (or higher) at temperatures of 75° to 250° C.

U.S. Pat. No. 3,239,566 also relates to the Rh and Ru catalyzed hydroformylation employing a tertiary organo-phosphine (e.g., trialkyl and tricycloalkyl phosphines, such as tricyclopentyl and tricyclohexyl phosphines) at 100° to 300° C. and total pressures of 690 to 13,800 kPa, using terminally- or internally-unsaturated olefins as feedstock.

U.S. Pat. No. 3,511,880 discloses the hydroformylation of alpha-olefins and internal-olefins employing a partially aqueous high boiling inert organic reaction medium containing a Group VIII noble metal biphyllic ligand complex as the catalyst and containing an alkaline material such as ammonium or alkali metal hydroxide. Suitable biphyllic ligands are said to include trialkyl phosphines, and tricyclohexyl phosphine and phenyl-diisopropyl phosphine are disclosed as suitable. Reaction temperatures of 50° to 200° C., and reaction pressures of 100–30,400 kPa are employed. U.S. Pat. No. 3,965,192 is similar in its disclosure to U.S. Pat. No. 3,511,880, as to suitable triorgano phosphines.

U.S. Pat. No. 3,527,809 relates to a process for hydroformylation of alpha-olefins using triaryl phosphines (having a $\Delta$HNP value of at least 425) in combination with rhodium catalyst, at a total pressure of less than 3100 kPa and at temperatures of 50° to 145° C. Triisopropyl phosphine ligand is disclosed to be an unsuitable ligand due to its low $\Delta$HNP value. Also excluded were trialkyl phosphines and tricycloalkyl phosphines.

U.S. Pat. No. 4,201,728 discloses highly selective alpha-olefin hydroformylation catalysts comprising a stabilized rhodium complex containing a bidentate ligand and a monodendate ligand, which is characterized by cylindrical cone angle $\theta$ of between about 135° and 150°. The reactions are carried out at from 25° to 150° C. and at 103 to 20,700 kPa.

Alpha-substituted alpha-olefins, similar to internal olefins, are known to be much less reactive than terminal olefins for hydroformylation. For example, U.S. Pat. No. 4,221,744 (column 15, lines 40–60) indicates that the internal olefin is relatively inert under the conditions of all of its preceding examples, and the relative inertness of alpha-substituted alpha-olefins (isobutylene) is also taught in U.S. Pat. No. 4,287,370 (under its conditions, in which a mixed butene feedstock is contacted with a rhodium triorganophosphine ligand system, in which the ligand can be trialkylphosphine (column 5, lines 29–30).

U.S. Pat. No. 3,576,881 (column 5, lines 20–23) teaches that biphyllic triorganophosphorus ligands having cycloaliphatic groups, do not form active catalyst species for Fe, Co and Rh catalyzed olefin hydroformylations. The reference, therefore, employs trialkyl and trialkoxy phosphorus ligands.

B. Fell et al., *Tetrahedron Letters* No. 29, pp. 3261–3266 (1968) conducted studies on olefin isomerizations during the hydroformylation of higher molecular weight olefins with complex cobalt and rhodium catalysts. Trialkyl phosphines were found to suppress olefin isomerization without suppressing hydroformylations, in hydroformylation of 1-octene and trans-octene-4 in an agitated autoclave at 20,270 kPa and 140° C. (using 1:1 CO:$H_2$) to greater than 90% theoretical yield, using $Rh_2O_3$ with either tricylcohexyl phosphine or tri-n-butyl phosphine (Table 2). N-hexenoic-3-acid-1-methyl ester was hydroformylated at 120° C. under similar conditions using a Rh catalyst system containing tricyclohexyl phosphine (Table 5). However, with four hours of reaction time, assuming complete conversion, the hydroformylation rates for tricyclohexyl phosphine (using a Rh concentration of 1.75 mmol Rh per mole of olefin charged) corresponded to a catalyst turnover of only 142.9 moles olefin/mole Rh/hour. Therefore, Fell et al. reported similar performance for tricyclohexyl phosphine and tri-n-butyl phosphine in Rh hydroformylation catalyst systems, no distinction in aldehyde production rates being observed. The Fell et al. experiments are also discussed in F. Asinger et al., *I&EC Prod. Res. & Dev.*, vol. 8, no. 2, 214 (1969) and E. R. Tucci, *I&EC Prod. Res. & Dev.*, vol. 8, no. 2, 215–26 (1969).

B. Fell et al., *J. Molec. Catalysis*, vol. 2, 211–218 (1977) investigated the hydroformylation of conjugated dienes using certain aliphatic tertiary phosphines (including tris-isopropyl phosphine) at specified conditions.

German Pat. No. 2,538,364, as abstracted in 85 Chem. Abs. 45,962m, reported no difference in results in the rhodium catalyzed hydroformylation of allyl alcohol with tris-triphenyl phosphine, tri-n-butyl phosphine, tricyclohexyl phosphine and 4-methyl benzene.

Van Leewen and Roobeek, *J. Organomet. Chem.*, vol. 258, pp. 343–350 (1983) investigated the hydroformylation of 2-alkyl-1-alkenes and cyclohexene with bulky phosphite ligands, and reported low rates of reaction when using tricyclohexyl phosphine as the ligand of the rhodium catalyst system.

U.S. Pat. No. 4,443,638 relates to a process for preparing alcohols from internal olefins including the step of hydroformylating internal olefins to aldehydes using a small amount of a recycled rhodium catalyst which is "ligand modified". Suitable ligands which are disclosed are the trialkylphosphites, tricyloalkyl phosphites, triarylphosphites, triarylphosphines, trialkyl phosphines, triarylstilbines and triaryl arsines. Temperatures of 145° to 180° C. and pressures of about 5,100 to 13,800 kPa are used in the hydroformylation. The recycled rhodium catalyst is separated from the hydroformylation reaction product by flash distillation, prior to the catalyst's recycle to the hydroformylation reactor.

European Patent Application No. 28,378 relates to an improved rhodium-catalyzed hydroformylation process wherein the catalyst stability is improved by use of a ligand selected from a branched chain alkyl diphenylphosphine, a branched chain dialkyl-phenylphosphine, a cycloalkyldiphenylphosphine, and a dicycloalkylphenylphosphine. European Patent Application No. 96,988 relates to a hydroformylation process for producing non-linear aldehydes from optionally substituted internal olefins, using a certain class of cyclic phosphite ligands.

A. A. Oswald et al., *Preprint of Papers, American Chemical Society* (Seattle Meeting, March 20-25, 1983), vol. 2, no. 2, pp. 191–208 reports the rhodium catalyzed hydroformylation of 1-butene using branched alkyl diphenyl phosphine ligands, including cyclohexyl diphenyl phosphine.

SUMMARY OF THE INVENTION

It has been surprisingly found that alpha-substituted alpha-olefins can be hydroformylated at a very rapid rate and in high selectivity to aldehyde product using a homogeneous rhodium catalyst system containing a highly sterically hindered tricycloalkyl phosphine ligand under mild process conditions.

The high rates of reaction achieved by the process of this invention are in excess of those which can be achieved by conventional rhodium triaryl phosphine catalyst systems which are thermally unstable at temperatures exceeding 145° C., and these rates are also surprisingly greatly in excess of those which can be achieved by use of tri-n-butyl phosphine under similar reaction conditions (contrary to the implications of B. Fell et al., *Tetrahedron Letters No.* 29, pp. 3261-3266, 1968).

These catalyst systems are surprisingly stable at high temperatures, with negligible degradation rates being observed in continuous rhodium catalyzed hydroformylations.

The discovery that these tricycloalkyl phosphines provide such high rates of hydroformylation is especially surprising since they are generally strong Lewis Bases, and from the prior art would be expected to give lower rates of reaction, since the phosphorus-rhodium bond strength is known to increase with increasing Lewis basicity of the phosphine ligand. The resulting ligand is therefore less labile and the Rh complex should, therefore, be expected to be less active. In contrast, it has been found that the rhodium-tricycloalkyl phosphine catalysts of this invention are more active under the reaction conditions disclosed herein than are rhodium tri-n-alkyl phosphines, even though tricyclohexyl phosphine is a more basic ligand.

It is theorized, without being bound thereby, that the sterically hindered tricycloalkyl phosphine ligands of this invention enable fundamental changes in catalyst structure to be maintained in the reaction medium, as a result of the steric crowding of the bulky phosphine ligands. The net result is that these catalysts have fewer phosphines and more carbon monoxide bound to the rhodium in the active form than do catalysts with smaller, less crowded phosphine ligands.

My findings regarding the increased rates are also contrary to the understanding of the prior art which qualitatively show that both rate and selectivity increase as the phosphine ligand is changed from a more basic alkyl phosphine to the less basic aryl phosphine. R. L. Pruett et al., *JO Chem*, vol. 34, 327 (1969); K. L. Oliver et al., *Am. Chem. Soc. Pet. Div. Prepr, Gen. Pap.*, vol. 14 (3), 47 (1969).

It has been further found that an increased hydrogen partial pressure has an activating, and hence beneficial effect on the catalyst system. In contrast, it has been taught that hydrogen partial pressures should be controlled to minimize unnecessary loss of excess hydrogen without any attendant benefit (U.S. Pat. No. 4,287,370). Also, activity has been found to be proportional to the total carbon monoxide and hydrogen pressure and has also surprisingly been found to be relatively independent of phosphine ligand concentration or phosphorus:rhodium molar ratios, again contrary to teachings in the prior art.

The bulky tricycloalkyl phosphines of this invention have been further found to exhibit a hydroformylation reaction rate which is essentially independent of ligand to Rh molar ratio (over the tested range from 15:1 to 80:1) and a less than first order dependence upon Rh concentration was observed.

DETAILED DESCRIPTION OF THE INVENTION

The olefins which are passed as feedstocks to the process of this invention contain terminal carbon-carbon double bonds and are substituted on the alpha carbon atom by a substituent which can comprise alkyl, aryl, alkaryl, aralkyl, cycloalkyl, —OC(O)X, —CHO, carboxylate (—C(O)OX, wherein X is alkyl of 1 to 20 carbon atoms) and the like. Therefore, the olefins comprise members selected from the group consisting of compounds of the formula (I):

wherein $R^1$ and $R^2$ can be the same or different and comprise a member selected from the group consisting of alkyl, aryl, alkaryl, aralkyl, cycloalkyl,

—CHO and carboxylate. Also useful are ethers of unsaturated alcohols and esters of unsaturated alcohols and/or acids. A preferred class of alpha-substituted alpha-olefins are alkyl-substituted aliphatic alpha-olefins having a total of from 4 to 20 carbon atoms per molecule wherein the alkyl substituent contains from 1 to 17 carbon atoms. Illustrative of suitable alpha-substituted aliphatic alpha-olefins are isobutylene, 2-methyl-1-butene, 2-methyl-1-heptene, 2-ethyl-1-hexene, 2-amyldecene-1, 2-propyl-1-heptene, 2,3-dimethyl-1-butene, 1-methyl-1-phenyl-ethylene(alpha methyl styrene), 1,1-diphenyl ethylene, methyl methacrylate, isopropenyl acetate, methacrolein, methacrylamide, and the like.

The alpha-substituted alpha-olefin may be supplied to the hydroformylation zone in substantially pure form, or as a mixture with one or more other alpha-olefins and/or inert materials such as saturated hydrocarbons, nitrogen, argon, and carbon dioxide. In mixtures containing one or more such alpha olefins, an internal olefin or unsubstituted alpha-olefin or both may also be present, in minor amounts. The saturated hydrocarbons will generally comprise hydrogenation by-products of the hydroformylation reaction, for example, isobutane, in the case of hydroformylation of isobutylene. Where present, the sum of such internal olefins and unsubstituted alpha-olefins will generally be employed in the amount of less than about 15 wt.%, and more generally less than about 5 wt. % of the total olefin feedstream.

As an example of a mixed internal/alpha-olefin stream, there may be mentioned the use of a mixed butenes hydrocarbon feedstock containing isobutylene and mixed propylene or butene dimerization products containing 2-ethyl-1-hexene, and 2-methyl-1-pentene. In this instance, the alpha-olefins butene-1 and isobutylene will be converted into the corresponding aldehydes, that is mainly normal-valeraldehydes and 3-methylbutyraldehyde respectively. In such mixed hydrocarbon feedstocks, again, the major olefin component is the internal olefin, e.g., butene-2.

The tricycloalkyl phosphine ligands ("L") which are employed in the process of the invention comprise ligands of the formula:

(II)

wherein "n" is an integer of 1–12, inclusive.

Exemplary ligands of formula (I) are tricyclopropylphosphine, tri-cyclobutylphosphine, tri-cyclopentylphosphine, tri-cyclohexylphosphine, tri-cycloheptylphosphine, tri-cyclooctylphosphine, tri-cyclononylphosphine, tri-cyclodecylphosphine, tri-cyclododecylphosphine and the like.

The preferred ligands are members selected from the group consisting of the following formula:

(III)

wheren n' is an integer of from 1 to 8, inclusive. Illustrative of such preferred ligands are tri-cyclohexyl phosphine, tri-cyclooctyl phosphine, tri-cyclopentyl phosphine and the like.

It is an important aspect of the present invention hydroformylation catalyst system that the ligand component is employed in a molar excess, and that the ligand has an atomic structure with a specific steric configuration in the stabilized catalyst complex, i.e., the steric parameter $\Theta$ of the ligand in the catalyst complex is an apex of at least 145°, preferably from 165° to 170°, and most preferably about 170°. By the term "steric parameter $\Theta$" is meant the apex angle of a cylindrical cone, centered 2.28 Å from the center of the group VA atom Q', which just touches the Van der Waals radii of the outermost atoms of the R' substituents of a symmetrical Q'R'$_3$ ligand [C. A. Tolman, *J. Amer. Chem., Soc.*, 92, 2953 (1970); Ibid, 92, 2956 (1970); and Ibid, 96, 53 (1974); C. A. Tolman, *Chem. Rev.*, vol. 77, no. 3, 313 (1977)].

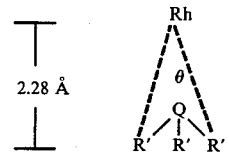

The steric parameters $\Theta$ apex angle of an unsymmetrical ligand (e.g., Q'R$^1$R$^2$R$^3$, where R$^1$, R$^2$ and R$^3$ are different hydrocarbyl groups) can be estimated from a knowledge of the cone angles of the corresponding symmetrical ligands Q'(R$^1$)$_3$, Q'(R$^2$)$_3$ and Q'(R$^3$)$_3$, on the basis of the formula:

$$\theta(Q'R^1R^2R^3) = \frac{2}{3}\left[\frac{\theta(Q^1R^1)_3}{2} + \frac{\theta[Q^1(R^2)_3]}{2} + \frac{\theta[Q^1(R^3)_3]}{2}\right] \quad (IV)$$

Catalyst Preparation

The present invention's catalysts can be prepared in situ in the hydroformylation reaction zone or, alternatively, can be prepared ex-situ and subsequently introduced into the reaction zone with the appropriate hydroformylation reactants. The most preferred catalysts are prepared by admixing one mole of suitable rhodium source with between about 10 to 100 mole of ligands L.

The amount of processing required for conversion of the rhodium metal depends on the nature of the initial rhodium source. Hence, if the rhodium in the starting material source is a salt in which rhodium is the cation moiety (e.g., a Rh$^{+3}$ valence state), at some stage in the catalyst preparation or in the hydroformylation process the rhodium metal must be reduced to the Rh$^{+1}$ valence state. The reduction is normally accomplished with hydrogen, or other reducing agents. When the rhodium source compound contains halogen, then a halide scavenger is employed in connection with the rhodium valence state reduction so as to eliminate the hydrogen halide as it is generated during the reduction step. This can be achieved by contact with H$_2$/CO in the hydroformylation process, or alternatively by employment of an equivalent source of hydrogen such as hydride (e.g., sodium borohydride).

In a preferred method of catalyst preparation, the rhodium source compound (e.g., a rhodium salt of a mineral acid or a carboxylic acid) is converted to a carbonyl derivative in a first step, followed by subsequent reaction of a rhodium carbonyl derivative with the ligands. If the primary rhodium source compound is already a carbonyl-containing compound than the initial carbonylation step can be eliminated.

Suitable rhodium sources which do not already comprised a carbonyl moiety in the molecule include the simple salts such as the halides (especially rhodium trichloride trihydrate), rhodium sulfate, rhodium nitrate, and rhodium carboxylates including the rhodium salts of simple carboxylic acids and dicarboxylic acids. Rhodium sources already containing carbonyl moiety in the molecule include (PPh$_3$)$_3$Rh(CO)H, (PPh$_3$)$_2$Rh(CO)Cl, Rh$_6$(CO)$_{16}$, Rh[CO]$_2$AcAc (rhodium dicarbonyl acetyl acetonate) and rhodium carbonyl chloride dimer (i.e., [Rh(CO$_2$)Cl]$_2$. The material known in the trade as "rhodium on carbon", which comprises a mixture of rhodium oxides of a rather complex nature on a carbon support, can also be employed. Hydridocarbonyl-tris(triphenylphosphine) rhodium (I) is a highly preferred rhodium source for catalyst preparations.

The various methods of preparing the present invention ligand stabilized rhodium catalysts can be summarized as follows: p (1) When the rhodium is initially in a noncarbonyl form, the rhodium is converted to a carbonyl derivative by reaction with carbon monoxide. Typical carbonylation procedures are described in "Inorganic Synthesis", vol. 8, 211 (1966).

The rhodium carbonyl compound is then combined with the ligand component of the catalyst system.

If hydrogen halide is generated during the catalyst preparation, a base is added as a halide scavenger. Alkaline borohydride is a versatile reagent for rhodium valence state reduction from Rh$^{+3}$ to Rh$^{+1}$, and for concomitant halide scavenging.

(2) When rhodium is initially available in the form of a carbonyl derivative, the rhodium carbonyl compound is reacted directly with the ligand to form the ligand stabilized rhodium catalyst. When the rhodium carbonyl derivative is a compound such as rhodium carbonyl chloride dimer, the interaction with the ligand is conducted in the presence of (1) a hydrogen chloride scavenger such as pyridine or sodium hydroxide, and (2) a hydride source such as hydrogen or a borohydride.

(3) Another alternative which is a convenient laboratory procedure is to form the rhodium carbonyl hydride by displacing triarylphosphine ligands from hydridocarbonyltris(triphenylphosphine) rhodium (I) with ligand:

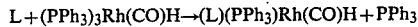

L+(PPh$_3$)$_3$Rh(CO)H→(L)(PPh$_3$)Rh(CO)H+PPh$_3$

This produces a complex with L as the ligand. In order to shift the equilibrium to increase the displacement of PPh$_3$, it is usually required to incorporate in the reaction medium an excess of ligand, e.g., 10 to 100 moles of L per mole of rhodium metal in the complex.

The catalyst preparation procedures described above are all conducted in the liquid phase and preferably in the presence of an inert solvent such as benzene or toluene. Suitable reaction temperatures are in the range between about 25° and 100° C.

Hydroformylation Conditions

As a general procedure, the catalyst system is first formed in a deoxygenated solvent medium in a hydroformylation reaction zone in a manner as described above. Excess ligand can perform as the solvent medium. The hydroformylation zone is pressured with hydrogen and carbon monoxide and heated to a selected reaction temperature. Internal olefin feed is then charged to the hydroformylation zone, and the reaction is conducted until the desired conversion yield and efficiency have been attained. The reaction can be performed in a batchwise, continuous or semi-continuous manner.

It is preferred that the temperature of the hydroformylation reaction be maintained in the range between about 80° and 200° C. For most of the internal olefin hydroformylation reactions, a reaction temperature between about 120° and 180° C. and a reaction time between about 0.5 and 4 hours is particularly preferred.

The pressure in the hydroformylation reaction zone is important to obtain the observed high rates of reaction, and the maximum pressure generally will be less than about 14,000 kPa to avoid increased expenses in pressure resistant equipment. Preferably, a total pressure within the range of from about 3,500 to 14,000 kPa, and more preferably from about 5,500 to 11,000 kPa will be used.

The ratio of hydrogen to carbon monoxide can vary broadly over a mole ratio range between about 0.2:1 and 5:1. The average mole ratio will vary between about 0.5:1 and 2:1. The quantity of hydrogen/carbon monoxide charged should be at least sufficient to satisfy the stoichiometric requirements of the internal olefin hydroformylation reaction.

Although it is not essential, an inert solvent can be employed as a hydroformylation reaction medium diluent. A variety of solvents can be used including ketones such as acetone, methyl ethyl ketone, methyl isobutyl ketone, acetophenone, and cyclohexanone; aromatics such as benzene, toluene and xylenes, halogenated aromatics including orthodichlorobenzene; ethers such as tetrahydrofuran, dimethoxyethane and dioxane; halogenated paraffins including methylene chloride; paraffinic hydrocarbons such as heptane; and the like.

It is an important aspect of the present invention that the hydroformylation process is conducted in the presence of excess ligand, and that the ligand component of the ligand stabilized catalyst has a steric parameter $\ominus$ apex angle of from about 165° to 170°, and most preferably from about 160° to 170°, in order to achieve optimum advantages in the practice of the invention process, i.e., highly selective and efficient conversion of alpha-substituted alpha-olefins to ensure sufficient ligand to overcome loss of ligand due to poisoning by trace impurities (such as O$_2$, S or halides), and to provide sufficient thermal stability to the catalyst to avoid plating out of Rh metal on equipment surfaces, particularly in catalyst recycle lines.

The sterically hindered ligands employed in this invention are provided in the hydroformylation medium in a mole ratio of between about 10 to 100 moles, preferably between about 15 and 80 moles, of the ligand per gram atom of rhodium metal. The rhodium concentration in the liquid reaction medium may vary from about 10 ppm or less up to about 1,000 ppm or more, calculated in each case as rhodium metal and on a weight-/volume basis. Typically, the rhodium concentration in the liquid reaction medium lies in the range of from about 40 ppm up to about 200 ppm, calculated as rhodium metal. For economic reasons, it will not usually be desirable to exceed about 500 ppm rhodium, calculated as metal, in the liquid reaction medium.

Without intending to be bound thereby, it is believed that complexed rhodium-catalyzed homogeneous hydroformylations involve a reaction mechanism in which the predominant form of the catalyst present under hydroformylation conditions, the catalyst reservoir, is a five coordinate Rh species such as complex VI, VII or VIII illustrated below, wherein "L" represents a triorganophosphine ligand. Complexes VI and VIII have been reported observed directly by $^{31}$P NMR spectroscopy under hydroformylation conditions with tristriphenylphosphine as ligand.

It has been postulated that the rate determining step for this hydroformylation reaction is the generation of four coordinate unsaturated complexes such as IX or X. Moreover, it was postulated that under conditions of high triphenyl phosphine concentrations, complex IX gives high selectivity to linear aldehyde product using alpha-olefin feeds, and that complex X is much less selective for linear aldehyde, versus branched aldehyde products.

It is believed that the precise form of the rhodium-complex in the hydroformylation reaction medium varies and its equilibrium can be illustrated as follows wherein again "L" is a triorganophosphine ligand.

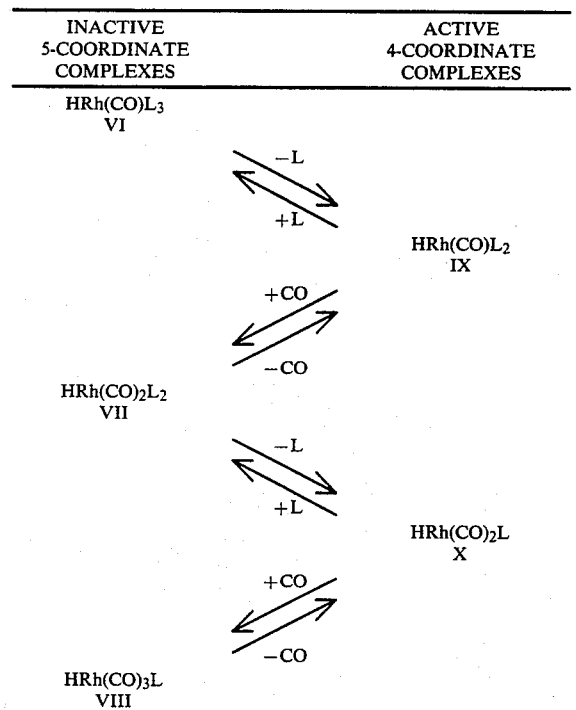

| INACTIVE 5-COORDINATE COMPLEXES | ACTIVE 4-COORDINATE COMPLEXES |
|---|---|

The relative predomination of a given rhodium complex VI-X is believed to be dependent upon a large variety of variables, namely, temperature, CO partial pressure, $H_2$ partial pressure, total reaction pressure, "L" ligand concentration and Lewis basicity of the ligand and steric size ($\theta$ cone angle 1 of the ligand). The lability of the "L" ligand, and thus the catalyst activity, is a function of the strength of the L-Rh bond, which is a function in itself of the Lewis basicity and the steric size of L. It has been found that increasing temperature or increasing CO pressure shifts the complex away from VI toward VIII and that oxo reaction rate increases as the complex is shifted from VI toward VIII. Also, increased CO and $H_2$ total pressures causes an increased stability of the rhodium complex as the complex is moved in the direction of VIII. In contrast, increased L concentration leads to a shift away from complex VIII toward complex VI, and results in an increase in the normal-to-iso isomer ratio in the product aldehyde with alpha-olefins.

The VI-VIII complexes are illustrated by the well known triphenyl phosphine-rhodium hydroformylation catalyst system (U.S. Pat. No. 3,527,809), which is commercially employed for linear alpha-olefin hydroformylations to form linear aldehydes.

Reaction variables that give high n/i product from butene-1, i.e. reaction variables that destabilize branched vs. linear intermediate complexes in the catalyst cycle, also produce slow rates of butene-2 hydroformylation because of the sterically hindered state of the branched intermediate. Thus, the observed relative inactivity of isobutene hydroformylation with conventional catalyst systems can be readily explained.

It can be seen that, to a large degree, the precise balancing of temperature, pressures and other reaction parameters is important to reaction rate, reaction selectivity and, importantly, to catalyst stability.

It has been surprisingly found that the bulky phosphine ligands of this invention, under the reaction conditions herein described emphasize the mono-phosphine bis-carbonyl rhodium hydride, $HRh(CO)_2L$ (i.e., complex X), over the bis-phosphine mono-carbonyl rhodium hydride (i.e., $HRh(CO)L_2$, or complex IX) and that this form (X) of the rhodium catalyst is stable at high temperatures and elevated pressures, and catalyzes the hydroformylation of alpha-substituted alpha-olefins at very rapid rates. In fact, the form of the catalyst IX is so deactivated when the ligand is tricyclohexyl phosphine that it has been isolated as a stable compound in contrast to the observed complex IX when the ligand is triphenyl phosphine.

In conventional Rh-triarylphosphine hydroformylation catalyst systems, increased CO partial pressure has an inhibiting effect on the oxo reaction rate, whereas increased $H_2$ partial pressure has an activating effect. These opposing effects result in a balance which, at a given $CO:H_2$ molar ratio (required to maintain oxo stoichiometry) tend to cancel one another out. In contrast, the bulky ligands of this invention have been surprisingly found to permit use of increased CO partial pressures as well as increased $H_2$ partial pressures without the attendant, conventional deactivation of the catalyst.

The amount of olefin fed to the reaction mixture depends on several factors, size of the reactor, the temperature of reaction, the total pressure, the amount of catalyst, etc. In general, the higher the olefin concentration is in the reaction medium, the lower usually will be the catalysts concentration that can be used to achieve a given conversion rate to aldehyde products in a given size of reactor. Since partial pressures and concentration are related, the use of higher olefin partial pressure leads to an increased proportion of the olefin in the product stream leaving the reaction mixture. Further, since some amount of saturated hydrocarbon may be formed by hydrogenation of the olefin, it may be necessary to purge part of the product gas stream in order to remove this saturated product before any recycle to the reaction zone, and this would be a source of loss for the unreacted olefin contained in the product gas stream. Hence, it is necessary to balance the economic value of the olefin lost in such a purge stream against the economic savings associated with lower catalyst concentration.

The aldehyde and alcohol products can be recovered from the reaction liquid by conventional means, as by distillation, gas stripping, flashing and the like, and the separated liquid catalyst mixture can be recycled to the hydroformylation reaction zone, along with make-up CO, $H_2$ and olefin (and make-up Rh and/or ligand as required).

Alternatively, the aldehyde and alcohol products can be removed as vapors from the hydroformylation reaction zone, condensed and treated for separation and purification using conventional procedure. Such a product flash off process alternative is known and is more fully described in U.S. Pat. No. 4,277,627, the disclosure of which is hereby incorporated by reference. If desired, the recovered aldehyde(s) can be conventionally hydrogenated (optionally after aldolization to form the corresponding dimer aldehyde(s)) to the alcohol, which in turn, can be purified using conventional technology and employed to esterify phthalic or other anhydrides to form plasticizers.

The make-up gases fed to the reaction medium will generally comprise the olefin, carbon monoxide, and hydrogen. Extrinsic poisons such as sulfur and sulfur-containing compounds, as well as halogens and halogen containing compounds, and the like, should be excluded from the make-up gases, since such materials can poison the catalyst and can deactivate the catalyst rather rapidly. Hence, it is desirable to reduce the amount of such poisons in all gases fed to the reaction. Of course, the amount of such poisons that can be tolerated is determined by the maximum acceptable rate of loss of activity of the catalyst, discussed above. If it is possible to permit some small amount of such poisons and still obtain a catalyst of desired stability, then such small amounts can be tolerated. It is generally desirable to reduce the amounts of such poisons in the make-up gases to below one part per million. This can be accomplished by methods known in the art.

The time of reaction, or residence period of the olefin in the reaction zone, is generally that time which is sufficient to hydroformylate the ethylenic bond of the alpha-olefin. As a general rule, the residence period in the reaction zone can vary from about several minutes to about several hours in duration and as apparent, this variable will be influenced, to a certain extent by the reaction temperature, the choice of alpha-olefin and catalyst, the concentration of free ligand, the total pressure, the partial pressure exerted by carbon monoxide and hydrogen, the conversion rate and other factors. As a general rule, it is desirable to achieve the highest possible conversion rate for the smallest amount of catalyst employed. Of course, the ultimate determination of a conversion rate is influenced by many factors including the economics of the process. A substantial advantaged of the present invention is that catalyst deactivation is minimized or substantially prevented while obtaining excellent conversion rates over prolonged periods of time.

The improved process of this invention can be further illustrated by reference to the following examples, wherein parts are by weight unless otherwise indicated.

EXAMPLE 1

A series of runs were performed in which the selected amount of rhodium dicarbonyl acetylacetonate and 2,2,4-trimethyl-1,3-pentane diol monoisobutyrate as a solvent and the selected amount of a triorganophosphine ligand were charged to a 300 cc stainless steel autoclave equipped with a stirrer under nitrogen atmosphere (10 psig) after which the autoclave was sealed and heated to the desired reaction temperature with stirring. At the reaction temperature, the indicated grams of alpha-substituted alpha-olefin was charged to the autoclave, the pressure was increased to the desired reaction pressure using a 1:1 $CO:H_2$ vol:vol ratio gas mixture. The reaction pressure was maintained by continuous addition of the $CO/H_2$ gas mixture. After 2 minutes, a sample was withdrawn and the product concentrations were determined by gas chromatography analysis. After 15, 30, 60, 120 and 180 minutes samples were also withdrawn and so analyzed. The products consisted of the indicated amounts of aldehyde and alcohol (formed by hydrogenation of product aldehyde), the olefin feed and isomers of the olefin feed.

The data thereby obtained are summarized in Table 1 below.

It will be obvious that various changes and modification may be made without departing from the invention and it is intended, therefore, that all matter contained in the foregoing description shall be interpreted as illustrative only and not limitative of the invention.

TABLE I

| Run No. | Olefin Feed (gms) | Phosphine Ligand (gms) | Ligand Cone Angle ($\theta$) | Solvent Weight (gms) | Reaction Temperature (°C.) (1) |
|---|---|---|---|---|---|
| 1-1 | 2-ethyl-1-hexene (60.0) | Triphenyl (0.656) | 145° | 90.0 | 110 (5) |
| 1-2 | 2-ethyl-1-hexene (60.0) | Tricyclohexyl (0.701) | 170° | 90.0 | 160 |
| 1-3 | 2,3-dimethyl-1-butene (5.0) | Tricyclohexyl (0.701) | 170° | 145.0 | 160 |
| 1-4 | 85% 2-ethyl-1-hexene 15% mixed octene isomers (370) | Tricyclohexyl (2.00) | 170° | (6) | 160 |
| 1-5 | iso-butylene (7) | Tricyclohexyl (14.4) | 170° | 600 | 140 |
| 1-6 | 2,2,4-trimethyl-1-pentene (9) | Tricyclohexyl (14.4) | 170° | 600 | 160 |

| Run No. | Reaction Rate Constant, k (2) | Alcohol + Aldehyde (3) | Olefin + Olefin Isomers (4) | Final Olefin Conversion | Run Time | ½ Life of Olefin (min) (2) |
|---|---|---|---|---|---|---|
| 1-1 | $2.06 \times 10^{-2}$ | 0.29% | 66.6% | 85.9% | 180 min. | 33.5 |
| 1-2 | $8.15 \times 10^{-2}$ | 20.81% | 34.1% | 85.4% | 120 min. | 8.5 |
| 1-3 | $19.3 \times 10^{-2}$ | 17.84% | 0% | 100% | 30 min. | 3.6 |
| 1-4 | N.A. | 9.63% | N.A. | 87.2% | 360 min. | N.A. |
| 1-5 | $1.5 \times 10^{-2}$ | 2.5% | N.A. | 47% (8) | 16 days | 46.2 |

TABLE I-continued

| 1-6 | 0.8 × 10⁻² | 25.0% | N.A. | 35% (8) | 6 days | 86.6 |

(1) Reaction conditions for Runs 1-1 through 1-3: 0.0129 g Rh(CO)₂ acetyl acetonate, 8270 kPa of CO and H₂ at 1/1 molar ratio, in a 300 cc stirred autoclave.
(2) Observed pseudo first-order rate constant determined at 50% conversion for the formation of combined aldehyde and alcohol in min.⁻¹.
(3) Wt. % alcohol of total alcohol and aldehyde formed at the end of the reaction.
(4) Wt. % olefin of total olefin and olefin isomers remaining at the end of the reaction.
(5) Triphenyl phosphine decomposition occurred at reaction temperatures above 120° C. at rates sufficient to invalidate rate data.
(6) Reaction conditions for Run 1-4: 0.100 g Rh(CO)₂ acetyl acetonate, 6,894 kPa of CO and H₂ at 1/1 molar ratio, 400 ml. n-hexane solvent in a 2,000 cc stirred autoclave.
(7) Reaction 1-5 was run in a continuous mode with catalyst solution recycle after product distillation, conditions: 0.351 g Rh(CO)₂ acetyl acetonate, 6,894 kPa of CO and H₂ at 1/1 molar ratio in a 2,000 cc stirred autoclave.
(8) Conversion per pass.
(9) Reaction 1-6 was run as per 1-5 except that 0.702 g Rh(CO)₂ acetyl acetonate was used.

What is claimed is:

1. In a process for hydroformylation of an alpha-substituted alpha-olefin selected from the group consisting of compounds of the formula:

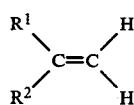

wherein R¹ and R² can be the same or different and comprise a member selected from the group alkyl, aryl, alkaryl, aralkyl, cycloalkyl,

—CHO and carboxylate, wherein X is alkyl of 1 to 20 carbon atoms in a hydroformylation reaction zone in the presence of a liquid rhodium triorgano phosphine catalyst system and in the presence of carbon monoxide and hydrogen to form the corresponding aldehydes, the improvement which comprises employing in the reaction zone a molar excess of at least one sterically hindered tricycloalkyl phosphine selected from the group consisting of compounds having the formula

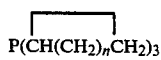

wherein "n" is an integer of 1-12, inclusive; and maintaining in the reaction zone a reaction temperature of from about 80° to 200° C., and a total carbon monoxide and hydrogen pressure of from about 3500 to 14,000 kPa, whereby improved hydroformylation reaction rates are achieved.

2. The improved process of claim 1 wherein said tricycloalkylphosphine comprises compounds of the formula

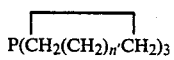

wherein "n'" is an integer of 1-8, inclusive.

3. The improved process of claim 1 wherein a temperature of from 120° to 180° C. and a pressure of from about 5,500 to 11,000 kPa is maintained in said reaction zone.

4. The improved process of claim 3 wherein said ligand is tricyclohexylphosphine.

5. The improved process of claim 1 wherein the mole ratio of H₂ to CO in the reaction zone is from about 0.2:1 and 5:1.

6. The improved process of claim 1 wherein the tricycloalkyl phosphine is employed in an amount sufficient to provide from about 10 to 100 moles of said tricycloalkyl phosphine per mole of rhodium in said reaction zone.

7. The improved process of claim 1 wherein R¹ is phenyl or alkyl of from 1 to 6 carbon atoms and R² is alkyl of from 1 to 6 carbon atoms.

8. The improved process of claim 1 wherein said alpha-substituted alpha-olefin comprises 2-ethyl-1-hexene.

9. The improved process of claim 4 wherein said alpha-substituted alpha-olefin comprises 2-ethyl-1-hexene.

10. A process for hydroformylation of an alpha-substituted alpha-olefin to form the corresponding aldehyde which comprises contacting an olefin selected from the group consisting of compounds of the formula:

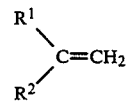

wherein R¹ and R² are the same or different and comprises a member selected from the group consisting of alkyl, aryl, alkaryl, aralkyl, cycloalkyl, hydroxy,

—CHO or carboxylate wherein X is alkyl of 1 to 20 carbon atoms, in a hydroformylation reaction zone in the presence of H₂ and CO and in the presence of a liquid reaction medium containing a rhodium organo phosphine hydroformylation catalyst wherein said organo phosphine is employed in a molar excess and comprises at least one tricycloalkyl phosphine of the formula:

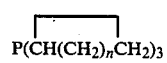

wherein "n" is an integer of 1 to 8, inclusive, and maintaining in the reaction zone a total carbon monoxide and hydrogen pressure of from about 3,500 to 14,000 kPa and a reaction temperature of from about 80° to 200° C.

11. The process according to claim 10 wherein said alpha-substituted alpha-olefin comprises at least one member selected form the group consisting of alkyl-substituted aliphatic alpha-olefins having a total of from 4 to 20 carbon atoms per molecule, wherein the alkyl substituent contains from 1 to 17 carbon atoms.

12. The process according to claim 11 wherein said tricycloalkyl phosphine comprises tricyclohexyl phosphine, tricyclooctyl phosphine or tricyclopentyl phosphine.

13. The process according to claim 10 wherein said tricycloalkyl phosphine ligand is employed in said liquid reaction medium in an amount of between about 10 and 100 moles of ligand per gram atom of said rhodium.

14. The process according to claim 13 wherein said rhodium catalyst is employed in said liquid reaction medium in an amount of from about 10 ppm to 500 ppm rhodium, calculated as the metal.

15. The process according to claim 14 wherein said alpha-substituted alpha-olefin comprises a member selected from the group consisting of isobutylene, 2-methyl-1-butene, 2-methyl-1-heptene, 2-ethyl-1-hexene, 2-amyldecene-1, 2-propyl-1-heptene, 2,3-dimethyl-1-butene, 1-methyl-1-phenyl-ethylene(alpha methyl styrene), 1,1-diphenyl ethylene, methyl methacrylate, isopropenyl acetate, methacerolein and methacrylamide.

16. A process for hydroformylation of an alpha-substituted alpha-olefin to form the corresponding aldehyde which comprises contacting an olefin selected from the group consisting of alkyl-substituted aliphatic alpha-olefins having a total of from 4 to 20 carbon atoms, wherein the alkyl substituent contains from 1 to 17 carbon atoms, in a hydroformylation reaction zone in the presence of $H_2$ and CO and in the presence of a liquid reaction catalyst and a molar excess of said organo phosphine, wherein said organo phosphine comprises at least one tricycloalkyl phosphine of the formula:

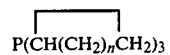

wherein "n" is an integer of 1 to 8, inclusive, and maintaining in the reaction zone a total carbon monoxide and hydrogen pressure of from about 3,500 to 14,000 kPa and a reaction temperature of from about 80° to 200° C.

17. The process according to claim 16 wherein said alpha-substituted alpha-olefin comprises a member selected from the group consisting of isobutylene, 2-methyl-1-butene, 2-methyl-1-heptene, 2-ethyl-1-hexene, 2-amyldecene-1, 2-propyl-1-heptene and 2,3-dimethyl-1-butene.

18. The process according to claim 17 wherein said tricycloalkyl phosphine comprises tricyclohexyl phosphine, tricyclooctyl phosphine or tricyclopentyl phosphine.

19. The process according to claim 18 wherein said tricycloalkyl phosphine ligand is employed in said liquid reaction medium in an amount of between about 10 and 100 moles of ligand per gram atom of said rhodium.

20. The process according to claim 19 wherein said rhodium catalyst is employed in said liquid reaction medium in an amount of from about 10 ppm to 500 ppm rhodium, calculated as the metal.

21. The process according to claim 20 wherein said alpha-substituted alpha-olefin comprises 2-ethyl-1-hexene.

22. The process according to claim 21 wherein said total carbon monoxide and hydrogen pressure is from about 5,500 to 11,000 kPa.

* * * * *